United States Patent
Strölin

(10) Patent No.: US 10,624,713 B2
(45) Date of Patent: Apr. 21, 2020

(54) SURGICAL LIGHT HAVING A VARIABLE LIGHT FIELD GEOMETRY

(71) Applicant: Karl Leibinger Medizintechnik GmbH & Co. KG, Mühlheim (DE)

(72) Inventor: Joachim Strölin, Rietheim (DE)

(73) Assignee: Karl Leibinger Medizintechnik GmbH & Co. KG, Mühlheim (DE)

( * ) Notice: Subject to any disclaimer, the term of this patent is extended or adjusted under 35 U.S.C. 154(b) by 137 days.

(21) Appl. No.: 15/751,344

(22) PCT Filed: Aug. 8, 2016

(86) PCT No.: PCT/EP2016/068892
§ 371 (c)(1),
(2) Date: Feb. 8, 2018

(87) PCT Pub. No.: WO2017/025512
PCT Pub. Date: Feb. 16, 2017

(65) Prior Publication Data
US 2018/0228569 A1    Aug. 16, 2018

(30) Foreign Application Priority Data
Aug. 13, 2015 (DE) .................. 10 2015 113 337

(51) Int. Cl.
*F21V 23/04* (2006.01)
*A61B 90/30* (2016.01)
(Continued)

(52) U.S. Cl.
CPC .............. *A61B 90/30* (2016.02); *F21S 2/005* (2013.01); *F21S 8/00* (2013.01); *F21S 8/043* (2013.01);
(Continued)

(58) Field of Classification Search
CPC . A61B 90/30; A61B 2090/309; F21V 23/045; F21V 23/0457
(Continued)

(56) References Cited

U.S. PATENT DOCUMENTS 3,437,803 A * 4/1969 Schafer ................ G02B 6/0005
362/8
4,196,460 A * 4/1980 Schreckendgust ...... F21S 10/02
362/2
(Continued)

FOREIGN PATENT DOCUMENTS

| CN | 101608778 A | 12/2009 |
| DE | 202007007054 U1 | 7/2007 |

(Continued)

OTHER PUBLICATIONS

Apr. 4, 2016—Office Action from the German Patent and Trademark Office (with machine English translation).
(Continued)

*Primary Examiner* — Eric S Gibson
(74) *Attorney, Agent, or Firm* — Banner & Witcoff, Ltd.

(57) ABSTRACT

The invention relates to a surgical light comprising a plurality of lights associated with a light group, which lights each produce a light beam extending along a longitudinal axis and are oriented and are arranged in relation to each other in such a way that the longitudinal axes of the light beams of the lights intersect in a common focal plane, wherein the lights of the light group can be supplied with current independently of each other such that a light field geometry produced by the lights in an illumination plane arranged at a distance from the focal plane can be adjusted.

12 Claims, 2 Drawing Sheets

Figure 4:
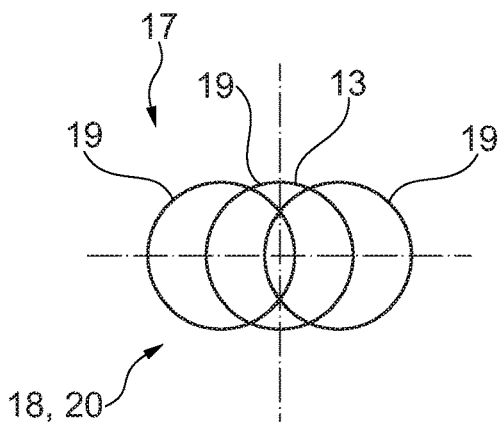

(51) Int. Cl.
  *F21S 8/00* (2006.01)
  *F21S 2/00* (2016.01)
  *F21S 8/04* (2006.01)
  *F21V 5/04* (2006.01)
  *F21W 131/205* (2006.01)
  *F21Y 115/10* (2016.01)
  *F21V 5/00* (2018.01)

(52) U.S. Cl.
  CPC .............. *F21V 5/04* (2013.01); *F21V 23/04* (2013.01); *F21V 23/045* (2013.01); *F21V 5/00* (2013.01); *F21W 2131/205* (2013.01); *F21Y 2115/10* (2016.08)

(58) Field of Classification Search
  USPC ............ 362/249.01, 249.02, 249.03, 249.06
  See application file for complete search history.

(56) References Cited

U.S. PATENT DOCUMENTS

| | | | | |
|---|---|---|---|---|
| 6,585,395 | B2* | 7/2003 | Luk | F21V 14/02 362/249.02 |
| 6,591,239 | B1* | 7/2003 | McCall | A61B 90/35 704/275 |
| 6,880,957 | B2* | 4/2005 | Walters | F21V 23/0442 250/205 |
| 7,465,065 | B2* | 12/2008 | Marka | F21S 2/005 362/232 |
| 7,562,999 | B2* | 7/2009 | Chen | F21V 5/048 362/239 |
| 7,841,741 | B2* | 11/2010 | Chan | H05K 1/189 362/249.04 |
| 8,201,966 | B2* | 6/2012 | Hall | F21V 5/008 362/231 |
| 8,300,906 | B2* | 10/2012 | Voelker | F21V 21/403 348/370 |
| 8,833,953 | B2* | 9/2014 | Schmid | F21V 21/403 362/33 |
| 9,016,916 | B2* | 4/2015 | Marka | A61B 90/35 362/572 |
| 9,289,269 | B2* | 3/2016 | Valteau | A61B 90/30 |
| 9,772,077 | B2* | 9/2017 | Kretschmann | F21S 8/00 |
| 10,057,451 | B2* | 8/2018 | Kim | G03B 15/14 |
| 10,180,238 | B2* | 1/2019 | Vu Thi | F21V 5/04 |
| 2003/0185009 | A1* | 10/2003 | Walters | F21V 23/0442 362/276 |
| 2005/0195599 | A1* | 9/2005 | Marka | F21S 2/005 362/232 |
| 2005/0195601 | A1* | 9/2005 | Marka | F21V 21/403 362/242 |
| 2006/0291204 | A1 | 12/2006 | Marka et al. | |
| 2008/0247163 | A1* | 10/2008 | Chen | F21V 5/048 362/237 |
| 2008/0273317 | A1* | 11/2008 | Kaletin | F21V 23/04 362/33 |
| 2008/0285820 | A1* | 11/2008 | Voelker | F21V 21/403 382/128 |
| 2009/0225539 | A1* | 9/2009 | Baldwin | G01N 21/47 362/227 |
| 2009/0318771 | A1* | 12/2009 | Marka | A61B 90/35 600/249 |
| 2009/0318772 | A1* | 12/2009 | Marka | A61B 90/35 600/249 |
| 2010/0002428 | A1* | 1/2010 | Hall | F21V 5/008 362/231 |
| 2010/0097802 | A1* | 4/2010 | Jurik | G02B 27/0994 362/235 |
| 2011/0037840 | A1 | 2/2011 | Hiltl et al. | |
| 2013/0188353 | A1* | 7/2013 | Nankil | F21V 21/14 362/235 |
| 2014/0066722 | A1* | 3/2014 | Marka | A61B 90/35 600/249 |
| 2014/0328045 | A1* | 11/2014 | Valteau | A61B 90/30 362/33 |
| 2016/0356458 | A1* | 12/2016 | Vu Thi | F21V 5/04 |
| 2017/0138562 | A1* | 5/2017 | Western | F21V 3/06 |
| 2018/0228569 | A1* | 8/2018 | Strolin | F21S 8/00 |
| 2018/0231227 | A1* | 8/2018 | Strolin | F21V 23/0457 |
| 2019/0154845 | A1* | 5/2019 | Holdsworth | G01T 1/161 |
| 2019/0183598 | A1* | 6/2019 | Senelier | F21S 4/22 |

FOREIGN PATENT DOCUMENTS

| | | |
|---|---|---|
| DE | 202007015823 U1 | 3/2008 |
| DE | 202008018046 U1 | 5/2011 |
| EP | 1568935 A1 | 8/2005 |
| EP | 1722157 A1 | 11/2006 |
| EP | 2136126 A1 | 12/2009 |
| EP | 2136128 A1 | 12/2009 |
| EP | 2283790 B1 | 10/2014 |

OTHER PUBLICATIONS

Sep. 21, 2016—International Search Report of PCT/EP2016/068892 (German with English Translation) and Written Opinion (German only).

Mar. 6, 2019—Chinese Office Action—Application No. 201680046646.0.

\* cited by examiner

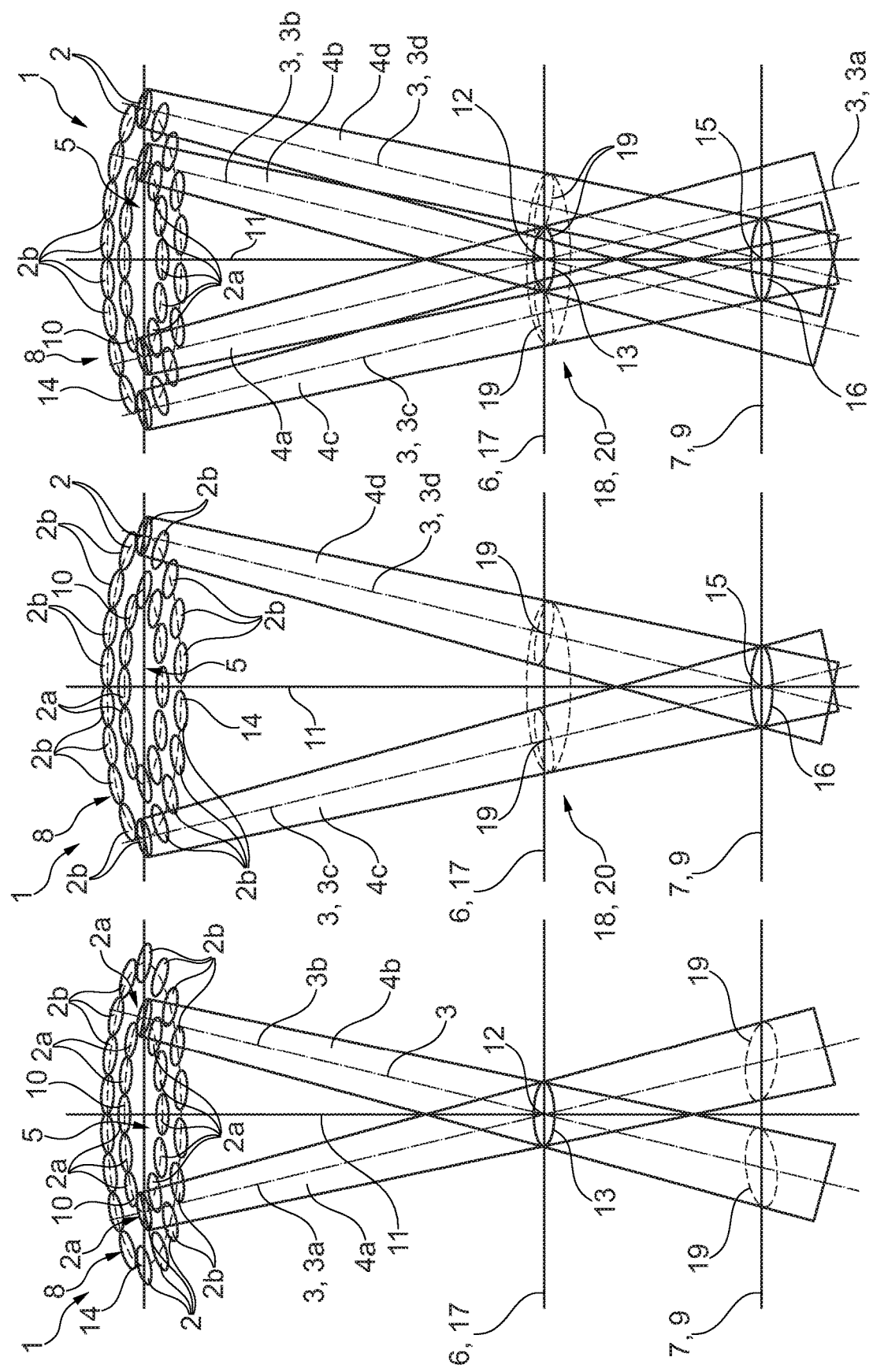

SURGICAL LIGHT HAVING A VARIABLE LIGHT FIELD GEOMETRY

CROSS-REFERENCE TO RELATED APPLICATIONS

This application is a U.S. National Stage application under 35 U.S.C. § 371 of International Application PCT/EP2016/068892 (published as WO 2017/025512 A1), filed Aug. 8, 2016, which claims priority to German Patent Application DE 102015113337.7, filed Aug. 13, 2015, each of which are hereby incorporated by reference in their entireties.

The invention relates to a surgical light for illuminating a wound area, comprising a plurality of lights associated with a light group which lights (in a state switched-on/supplied with current) each produce a light beam extending along a longitudinal axis and are oriented and arranged in relation to each other in such way that the longitudinal axes of the light beams of the lights intersect in a common focal plane.

A generic state of the art is known, for example, from EP 2 136 128 A1 comprising a surgical light comprising a light member having a central axis including at least two lamps having bundled light beams. An axis of individual light beams is focused on a point on a central axis, with a distance of the respective points from the light member in the direction of the central axis being different.

It has turned out that the surgical lights known from the state of the art are still relatively difficult to be adapted or cannot be adapted at all to the individual surgical areas especially with respect to the illumination. Primarily an adaptation of the illumination to wound areas varying during the operation is difficult to realize in this way. Since in the case of wound areas varying in shape all lights of the respective group have to be lightened or shaded in the known designs, it is a drawback that then the entire area in the illumination plane is evenly lightened or shaded. This is undesired, however, especially when the wound area takes a shape deviating from a circular formation and extends approximately in elongate shape. For in that case also the skin areas laterally adjacent to the elongate wound area are excessively lighted up, which may even result in blinding the operating surgeon, or the wound area is not sufficiently highlighted, which renders the wound area to be difficult to discern.

Therefore, it is the object of the present invention to eliminate these drawbacks known from the state of the art and to provide a surgical light which is intended to enable the wound area to be evenly illuminated independently of the shape of the respective wound area of the body being in surgery.

According to the invention, this object is achieved by the fact that the lights of the light group can be supplied with current (i.e. electrically supplied/actuated) independently of each other so that a light field geometry generated by the lights of the light group (i.e. by the light beams of the lights) can be adjusted in an illumination plane arranged at a distance from the focal plane.

In accordance with the invention, this enables an individual geometrical adjustment of the total light field produced which is produced by the light beams of the individual lights (also referred to as single lights) of the light group. This allows the resulting total light field to be adjusted in any way and "rotated" not only in circular shape but also in further shapes such as an oval or elongate shape. Such total light field may even be "rotated" by actuating individual lights of the light group about 360°, which allows to optimally adapt the light field to the wound area.

Further advantageous embodiments are claimed in the subclaims and will be illustrated in the following.

It is of further advantage when plural first lights are associated with a first light group and plural second lights are associated with a second light group, with the longitudinal axes of the light beams of the first lights intersecting in a first common focal plane and the longitudinal axes of the light beams of the second lights intersecting in a second common focal plane arranged at a distance from the first focal plane. This helps to realize a reliable illumination in plural planes. The first focal plane forms e.g. a (second) illumination plane of the second planes, while the second focal plane forms a (first) illumination plane of the first lights.

It is advantageous in this context when both the (first) lights of the first light group and the (second) lights of the second light group can be supplied with current/electrically actuated independently of each other so that the light field geometry produced on the respective illumination plane (first or second illumination plane) can be adjusted by the lights of each (first or second) light group. Therefrom it is resulting that the light field geometries of the light groups can be adapted even more individually.

It is of further advantage when the (first) lights of the first light group and/or the (second) lights of the second light group are arranged in a common light receiving member. This helps to fix the position of the individual lights of the different light groups relative to each other.

It is also useful when the lights associated with a light group (i.e. the (first) lights of the first light group and/or the (second) lights of the second light group) each are formed of a (preferably individually formed) light module comprising an LED. This helps to adjust the respective total light field/the respective light field geometry in an especially simple manner, with each light forming only one light spot (i.e. a substantially circular/oval partial light field) which can be switched on and, resp., off. By activating plural lights arranged along a longitudinal axis (of the same or a different light group) a chain of light spots arranged next to each other or partly overlapping each other is resulting. In this way an especially individual adjustment can be realized.

It is further advantageous when an independent (preferably adjustable) lens/optical lens system is associated with each of the lights associated with a light group (i.e. with the (first) lights of the first light group and/or the (second) lights of the second light group). The lens is equally part of the light module of the light. This allows especially simple control of the individual lights, wherein the focal width/focus of the lights can be individually adjusted.

In this context, it is also useful when the lights associated with a light group (i.e. the (first) lights of the first light group and/or the (second) lights of the second light group) can be adjusted independently of each other as to their brightness/illuminance. This helps to realize an even more individual adjustment of the resulting total light field.

Moreover, it is advantageous when at least several of the lights associated to the one light group (i.e. several of the (first) lights of the first light group and/or several of the (second) lights of the second light group) are different from each other by their luminous color. This allows to adjust also the resulting total light field as to color by individually controlling/supplying current to the lights.

In addition, it is also advantageous when the lights associated with one light group (i.e. the (first) lights of the first light group and/or the (second) lights of the second light group) are arranged next to each other in ring shape. Thus, all lights simply have to be arranged around the central axis of the surgical light inclined at an equal angle with the central axis. This helps to further facilitate the design.

In this context, it is especially useful, when the first lights associated with the first light group are arranged to be spread along a first ring-shaped peripheral line (with respect to a central axis of the surgical light) and the second lights associated with the second light group are arranged to be spread along a second ring-shaped peripheral line (with respect to a central line of the surgical light). This allows to form the total light field in as many different rotary positions as possible.

When the first peripheral line is arranged inside the second peripheral line, the constructional design of the surgical light is further facilitated.

When a (central) control unit that is electrically connected to each light associated with a light group (i.e. to each (first) light of the first light group and/or to each (second) light of the second light group) is provided in the surgical light, the light field geometries can be switched over by a particularly direct connection.

Further it is advantageous when an operating unit is provided by means of which the light field geometry is adjustable. This enables individual adjustment by the operating surgeon.

When the operating unit further includes a speech recognition unit, the total light field/the light field geometry of the surgical light can be adjusted also individually directly without touching the operating unit. This helps to further improve hygiene.

In this context, it is of further advantage when the operating unit is connected to the control unit by means of a wired or wireless data communication. This will further facilitate operation.

Figure 5:
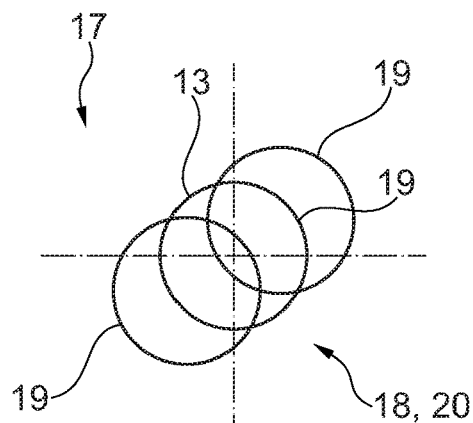
Figure 6:
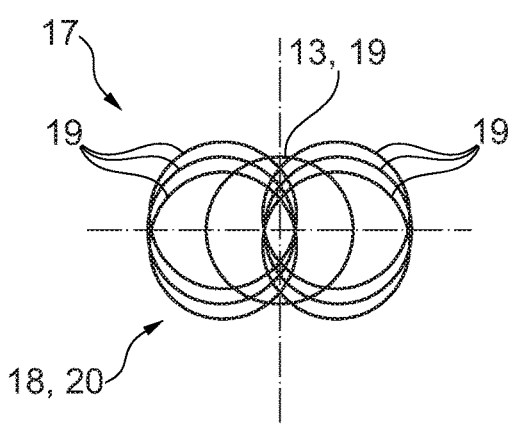
Figure 7:
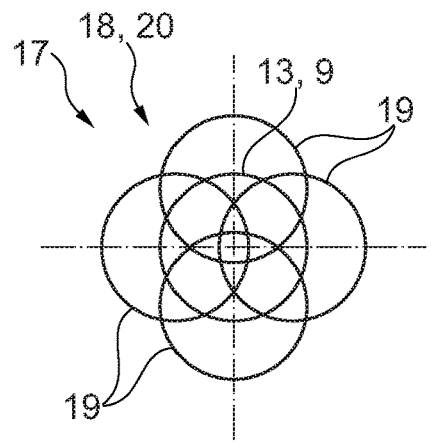
Figure 8:
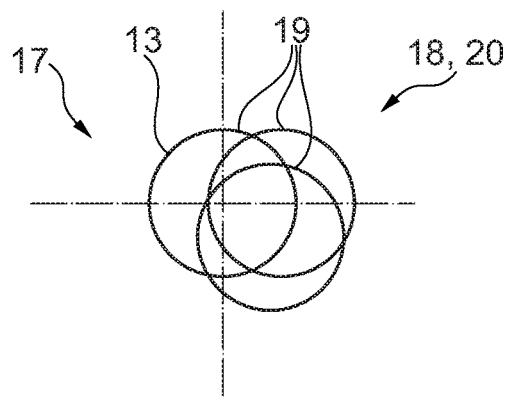

Hereinafter the invention shall be illustrated in detail by way of Figures, wherein:

FIG. 1 shows a schematic side view of a surgical light according to the invention in accordance with an advantageous embodiment, wherein the light beams of two first lights associated with a first light group are evident and especially the joint intersection thereof in the first focal plane is emphasized, while all of the (second) lights associated with a second light group are switched off, FIG. 2 shows a schematic side view of the surgical light according to FIG. 1, wherein now all of the first lights of the first light group are switched off, and instead two second lights of the second light group are switched on, and in turn the common intersection of the light beams thereof is evident in a second focal plane arranged at a distance from the first focal plane, FIG. 3 shows a schematic side view of the surgical light according to FIGS. 1 and 2, wherein now both two (first) lights of the first light group and two (second) lights of the second light group are switched on and the overlapping partial light fields of the light beams of the lights in the first focal plane are clearly visible, FIG. 4 shows a schematic top view onto an illumination plane in which the lights of the first and second light groups of the surgical light are controlled such that a resulting (total) light field is resulting which extends substantially linearly and preferably along a horizontal axis, FIG. 5 shows a top view onto the illumination plane according to claim 4, wherein now the lights of the first and second light groups are controlled such that an elongate total light field "rotated" by 45° as compared to FIG. 4 is resulting, FIG. 6 shows a top view onto the illumination plane according to FIG. 4, wherein now the lights of the first and second light groups are controlled so that a substantially H-shaped total light field is resulting, FIG. 7 shows a top view onto the illumination plane according to FIG. 4, wherein now the lights of the first and second light groups are controlled such that a substantially cross-shaped total light field is resulting, and FIG. 8 shows a top view onto the illumination plane according to FIG. 4, wherein now the lights of the first and second light groups are controlled such that a substantially triangular total light field is resulting.

The Figures are merely schematic and serve exclusively for the comprehension of the invention. Like elements are provided with like reference numerals.

The surgical light 1 according to the invention is especially clearly evident in FIG. 1 initially in its schematic design. The surgical light 1 in a usual way serves for illuminating/lighting an object, such as a human being, present on a treatment table. The surgical light 1 therefore is designed for illuminating an operating area, i.e. a wound area, on said object.

The surgical light 1 includes a plurality of individual lights 2. Each light consists of one single light module which, as to material, is formed separately from the residual lights 2. The light module in turn comprises an LED lamp/bulb/an LED light and a pertaining lens/optical lens system. The lights 2 only include one LED at a time in their light module. Also, each light module includes respective reflectors and, resp., devices for bundling the light emitted by the LED which light exits the light module on the lens side in the form of a light beam 4. Thus, each light 2 in a state switched-on/supplied with current forms a light beam 4 extending along a longitudinal axis 3. In other words, each light 2 and, resp., each light module of the light 2 produces a light beam 4.

In FIG. 1, schematically two first lights 2a associated with a first light group 5/lens group are switched on. The first light group 5 in this configuration consists not only of two but of more than two first lights 2a. In total, in the first light group 5 twelve first lights 2a are comprised. In further configurations, the number of the first lights 2a of the first light group 5 is also more than twelve or less than twelve, however.

The first lights 2a of the first light group 5 are arranged along a ring-shaped/circular ring-shaped peripheral line hereinafter referred to as first peripheral line 10. The first peripheral line 10 is arranged centrically with respect to an imaginary central axis 11 of the surgical light 1. During operation, the central axis 11 of the surgical light 1 forms the central axis 11 of a light receiving member of the surgical light 1 not shown here in detail for the sake of clarity. The light receiving member is the member on which the plurality of individual lights 2 is received/fastened. As a consequence, all of the lights 2 are fastened on said light receiving member. Moreover, the central axis 11 also is the axis that is present in the center of the light receiving member of the surgical light 1 and substantially extends along a handle of the surgical light 1 not described here in detail for the sake of clarity. In particular, the central axis 11 is the axis along which a journal-shaped grip portion of the handle that can be touched by the operating surgeon is extending.

Thus, the first lights 2a of the first light group 5 are arranged/stringed next to each other like a chain in a peripheral direction with respect to the central axis 11. All of the first lights 2a are aligned at an angle relative to the central axis 11 such that all of the longitudinal axes 3 thereof (the longitudinal axes 3 are the axes along which the light beam 4 is extending) intersect in a common intersection, here referred to as first intersection 12, that is present in a common first focal plane 6. All of the longitudinal axes 3 of the first lights 2a therefore have the same angle with the central axis 11. From the light module of the lights 2a the respective light beam 4 therefore extends always to the central axis 11 so that the common focus/intersection—first intersection 12—forms in the first focal plane 6. Since all first lights 2a of the first light group 5 intersect/overlap/cover each other in their switched-on state in said common first intersection 12 provided in the first focal plane 6, they form a common first round focal light field 13. The first focal light field 13 has a maximum first diameter of approx. 300 mm.

In FIG. 1, schematically two first lights 2a opposing each other relative to the central axis 11 are switched on so that one of the first lights 2a produces a first light beam 4 extending along a first longitudinal axis 3a and another first light 2a arranged to be offset by about 180° along the first peripheral line 10 forms a second light beam 4b extending along a second longitudinal axis 3b. Up to the first intersection 12 the two light beams 4a, 4b extend toward each other and, from a side of the first focal plane 6 facing away from the surgical light 1, said two light beams 4a and 4b then in turn extend away from each other, when viewed at the same angle (relative to the angular amount) between the respective longitudinal axis 3a, 3b relative to the central axis 11.

In a first illumination plane 7 arranged at a distance from the first focal plane 6, also simply referred to as illumination plane, each of the light beams 4a and 4b of the two first lights 2a forms/illuminates a partial light field 19.

As is evident in interaction with FIG. 2, apart from the first group/light group 5 of the first lights 2a a second light group 8/lens group is provided which in turn includes a plurality of the lights 2. The lights 2 referred to as second lights 2b of the second light group 8 have the same design and function as the first lights 2a. Thus, also each of the second lights 2b includes a light module comprising only one LED and one lens associated with said LED.

The second lights 2b of the second light group 8 are arranged radially outside the first lights 2a of the first light group 5, when viewed relative to the central axis 11. The second lights 2b, too, are arranged circularly next to each other on a peripheral line hereinafter referred to as second peripheral line 14. Hence also the second lights 2b are arranged in the peripheral direction of the central axis 11. Consequently, the second peripheral line 14 has a larger diameter than the first peripheral line 10.

Also, in the second light group 8 in turn not only two (second) lights 2b but more than two (second) lights 2b are used. In total, eighteen second lights 2b are contained in the second light group 8 and are stringed to each other in chain structure along the circular second peripheral line 14. However, in further configurations, also a different number of second lights 2b, such as more than eighteen or less than eighteen, is realized in the second light group 8. In addition, it is outlined that each of the lights 2a and 2b of the two first and second light groups 5 and 8 need not absolutely have a circular arrangement extending along a circular peripheral line 10, 14. It is also imaginable to arrange the light groups 5, 8 in a different way without deviating from the inventive idea.

Referring to FIG. 2, it is evident that all of the second lights 2b are in turn oriented toward the central axis 11. All second lights 2b again enclose an angle with the central axis 11 with their longitudinal axes 3 of the light beams 4. The longitudinal axes 3 of all second lights 2b take the same angle with the central axis 11.

In FIG. 2, again two switched-on lights 2b are schematically evident which are substantially opposed to each other by 180° relative to the second peripheral line 14. One of the two second lights 2b produces a light beam 4 referred to as third light beam 4c that extends along the third longitudinal axis 3c. The other of the two second lights 2b in turn produces, when being switched on, a fourth light beam 4d extending along a fourth longitudinal axis 3d. The two second lights 2b are adapted to each other so that their longitudinal axes 3c and, resp., 3d intersect in a common focal point/intersection—hereinafter referred to as second intersection 15—. Said second intersection 15 is located in a second focal plane 9 which is arranged at a distance from the first focal plane 6. Furthermore, not only the longitudinal axes 3c, 3d of the two second lights 2b switched on in FIG. 2 but all of the second lights 2b included in the second light group 8 intersect with their longitudinal axes 3 in said common second intersection 15 in the second focal plane 9.

Each focal plane 6 and, resp., 9 in this configuration is a normal plane relative to the central axis 11. In this embodiment, the second focal plane 9 forms the first illumination plane 7 of the first light group 5. The first focal plane 6 in turn forms a (second) illumination plane 17 for the second light group 8; therefore, the two light beams 4c, 4d of the two second lights 2b in this second illumination plane 17 again form two partial light fields 19 arranged at a distance from each other. Since all second lights 2a intersect/overlap/cover each other, when being switched on, in said common second intersection 15, said lights form a common (second) round focal light field 16 in the second focal plane 9. The second focal light field 16 has a maximum second diameter of about 150 mm. In a second illumination plane 17 at a distance from the second focal plane 9 which corresponds to the first focal plane 6 here, the two lights 2b thus form the round partial light fields 19 arranged at a distance from each other.

As is further evident, the first focal plane 6 is arranged more closely to the surgical light 1, i.e. to the light receiving member of the surgical light 1, than the second focal plane 9, when viewed along the central axis 11. Therefore, the first focal plane 6 has a smaller distance along the central axis 11 relative to the surgical light 1/the light receiving member than the second focal plane 9. In an especially advantageous embodiment, the distance of the first focal plane 6 along the central axis 11 from the surgical light 1/from the light receiving member amounts to 1 m and the distance of the second focal plane 9 along the central axis 11 relative to the surgical light 1/to the light receiving member amounts to 1.20 m, especially preferred to 1.40 m.

For illustration purposes, in FIG. 3 the two first lights 2a switched on in FIG. 1 and the two second lights 2b switched on in FIG. 2b are simultaneously actuated once again so that an elongate total light field 20 is resulting especially in the first focal plane 6 corresponding to the second illumination plane 17 but also in the second focal plane 9 corresponding to the first illumination plane 7. Thus, the total light field 20 is formed, in response to the first and/or second lights 2a, 2b supplied with current, in a particular light field array/light field geometry 18, with the light field geometry 18 (i.e. the geometry of the total light field 20)/the total light field 20 resulting from the individual partial light fields 19 of the individual lights 2a, 2b.

According to the invention, the individual lights 2a and, resp., 2b of the first light group 5 and of the second light group 8 can be supplied with current, i.e. electrically controlled/actuated, independently of each other within the group as well as between the groups so that the produced total light field 20 can be geometrically adjusted at will in the respective illumination plane 7, 17, for example. In this context, adjustment of the geometry is understood to be both a variation of the shape and, resp., the proportions of the total light field 20 (i.e. of the light field geometry 18) and a variation of the orientation of the total light field 20 (i.e. of the light field geometry 18) inside the illumination plane 7, 17. Different possible light field geometries 18 are illustrated in FIGS. 4 to 8.

For controlling the individual lights 2, in the surgical light 1, viz. inside the light receiving member, a central control unit not shown here in detail for reasons of clarity is provided which is electrically connected to the (first) lights 2a of the first light group 5 and is electrically connected to the (second) lights 2b of the second light group 8. The control unit is preferably also equipped by means of plural luminance sensors which are arranged, for example, in the light receiving member or in the handle device of the surgical light 1. The luminance sensors detect the just actually realized luminance in a wound area and thus provide the control unit with signals allowing to calculate whether the illumination of the wound area is possibly too bright or too dark. Thus, the control unit may generate a control command that is transmitted to the light groups 5, 8 and dims/switches off or lightens/switches on individual lights 2 or all lights. Also, said luminance sensors in turn allow to draw a conclusion therefrom as to which light field geometry 18, e.g. according to FIGS. 4 to 8, is most suited for the respective wound area.

It is further pointed out that the lights 2a and, resp., 2b of the first light group 5 and/or of the second light group 8 can be controlled/adjusted independently of each other as to brightness/illuminance. In addition, the lights 2a and, resp., 2b of the first light group 5 and/or of the second light group 8 can be operated/switched on and off independently of each other. While, e.g., a single one of the first lights 2a has a first brightness/illuminance, it is possible that a second one of the first lights 2a has a different brightness/illuminance, e.g. a higher brightness/illuminance.

Also, the lights 2a and, resp., 2b of the individual light groups 5 and, resp., 8 may differ from each other or between the groups as to their luminous color. While e.g. some of the first lights 2a produce a bluish partial light field 19, the others of the first lights 2a produce an orange partial light field 19.

In FIG. 4, an exemplary first light field geometry 18 is shown in an illumination plane corresponding to the first illumination plane 7. Here the first lights 2a and the second lights 2b (in a first control state of the control unit) are actuated so that three partial light fields 19 are resulting, wherein at least the central partial light field 19 at the same time is the second focal light field 16 (configured by the second lights 2b). The partially overlapping arrangement of the partial light fields 19 results in an elongate total light field 20. The total light field 20 thus forms an elongate first light field geometry 18.

In FIG. 5 illustrating a second light field geometry 18 in the first illumination plane 7, the first lights 2a and the second lights 2b are actuated/supplied with current (in a second control state of the control unit) so that three partial light fields 19 extend along an imaginary axis of extension and thus in turn produce an elongate (second) light field geometry 18. However, first lights 2a unlike those in FIG. 4 are switched on so that the second light field geometry 18 is rotated relative to the first light field geometry of FIG. 4, viz. rotated anti-clockwise by about 45°.

In FIG. 6, apart from the first lights 2a and the second lights 2b (in a third control state of the control unit) further lights 2 of other light groups are switched on, which other light groups are not shown here in detail for reasons of clarity, but function as the first light group. In this way, an H-shaped total light field 20 composed of seven partial light fields is produced. Thus, the total light field 20 includes a H-shaped third light field geometry 18.

In FIG. 7 the first lights 2a and the second lights 2b are actuated/supplied with current (in a fourth control state of the control unit) so that a cross-shaped fourth light field geometry 18 is formed.

In FIG. 7 the first lights 2a and the second lights 2b are actuated/supplied with current (in a fifth control state of the control unit) so that a triangular fifth light field geometry 18 is formed.

Furthermore, an operating unit is connected to the control unit. The operating unit serves for adjusting a light field geometry 18 desired by the operating surgeon/the user. The operating unit is connected to the control unit e.g. by means of a wired or wireless data communication, possibly "Bluetooth" data communication/connected to transmit data.

In another configuration, the operating unit also comprises a speech recognition unit which enables the light field geometry 19 to be adjustable via speech input. In addition, it is possible to operate the operating unit via an "app" installed on a mobile equipment such as a smartphone or a tablet PC and constituting a type of slide control by means of which the light geometry 18 can be adjusted.

In other words, the surgical light 1 according to the invention is equipped with a plurality of light sources (LEDs (in other words: light diode/light-emitting diode) in lights 2/light module of the lights 2). Each light source 2 includes an optical system. The light sources 2 are LEDs. All light sources 2 are oriented toward the main/central axis 11 of the surgical light 1. A part A of the light sources (first lights 2a of the first light group 5) arranged in the center of the surgical light 1 bundle the light at a distance X of the surgical light 1 from the illuminated field, e.g. at a distance of 1 m (in a first focal plane 6). A second part B of the light sources (second lights 2b of the second light group 8) arranged around the first part 5 of the light sources 2a bundle the light at a larger distance Y, e.g. at a distance of 1.4 m (in a second focal plane 9). That is to say: FIG. 1: light from part A→small light field at a distance of 1 m. FIG. 2: light from part B→small light field at a distance of 1.4 m. FIG. 3: light from part A+light from part B produce a large light field at a distance of 1 m so that the light from part B is supplemented by the light from part A. Equally, the depth illumination is improved in this way, as at the same time a type of focal cascade forms by the production of a light field (focal light fields 13, 16) at the distance X and Y.

This principle can be ideally extended by further light areas C and thus further light fields and distances Z. The elongate/oval light field (total light field 20) is produced by controlling individual light sources (first lights 2a) from the area A and of light sources from the area B (second lights 2b) which are located in a longitudinal orientation. When each LED of the surgical light 1 is individually controlled (matrix control), it is possible to vary the longitudinal orientation and to rotate the elongate light field 20 in the grid of the LED array—FIGS. 4 and 5. Also further patterns according to FIGS. 6 and 7 as well as eccentrically according to FIG. 8 are possible.

REFERENCE NUMERALS 1 surgical light
2 light
2a first light
2b second light
3 longitudinal axis
3a first longitudinal axis
3b second longitudinal axis
3c third longitudinal axis
3d fourth longitudinal axis
4 light beam
4a first light beam
4b second light beam
4c third light beam
4d fourth light beam
5 first light group
6 first focal plane
7 first illumination plane/illumination plane
8 second light group
9 second focal plane
10 first peripheral line
11 central axis
12 first intersection
13 first focal light field
14 second peripheral line
15 second intersection
16 second focal light field
17 second illumination plane
18 light field geometry/light field arrangement
19 partial light field
20 total light field

The invention claimed is:

1. A surgical light comprising a plurality of lights associated with several light groups, wherein a plurality of first lights are associated with a first light group and a plurality of second lights are associated with a second light group, and wherein lights of the same light group each produce a light beam extending along a longitudinal axis and are oriented and arranged in relation to each other in such way that longitudinal axes of light beams of lights of the same light group intersect in a common focal plane, so that longitudinal axes of light beams of the first lights intersect in a first common focal plane and longitudinal axes of light beams of the second lights intersect in a second common focal plane arranged at a distance from the first focal plane,
wherein a control unit is provided which is electrically connected to each first light of the first light group and to each second light of the second light group such that the first lights of the first light group and the second lights of the second light group can be supplied with current independently of each other such that a light field geometry produced by the first lights and the second lights in an illumination plane arranged at a distance from the focal plane can be adjusted, and
wherein the control unit is configured to actuate the first lights and the second lights in at least a first control state by forming an elongate total light field.

2. The surgical light according to claim 1, wherein the first lights of the first light group and/or the second lights of the second light group are arranged in a common light receiving member.

3. The surgical light according to claim 1, wherein each of the first lights associated with the first light group or each of the second lights associated with the second light group is formed of a light module comprising an LED.

4. The surgical light according to claim 1, wherein a respective separate lens is associated with each of the first lights associated with the first light group or with each of the second lights associated with the second light group.

5. The surgical light according to claim 1, wherein the first lights associated with the first light group or the second lights associated with the second light group can be adjusted independently of each other as to their illuminance.

6. The surgical light according to claim 1, wherein at least several of the first lights associated with the first light group or at least several of the second lights associated with the second light group are different from each other by their luminous color.

7. The surgical light according to claim 1, wherein the first lights associated with the first light group or the second lights associated with the second light group are arranged next to each other in a ring shape.

8. The surgical light according to claim 7, wherein the first lights associated with the first light group are arranged to be spread along a first ring-shaped peripheral line and the second lights associated with the second light group are arranged to be spread along a second ring-shaped peripheral line.

9. The surgical light according to claim 8, wherein the first peripheral line is arranged inside the second peripheral line.

10. The surgical light according to claim 1, wherein an operating unit is provided and configured to adjust the light field geometry.

11. The surgical light according to claim 10, wherein the operating unit includes a speech recognition unit.

12. The surgical light according to claim 10, wherein the operating unit is connected to the control unit by a wired or wireless data communication.

* * * * *